United States Patent
Freyman et al.

(10) Patent No.: US 7,517,338 B2
(45) Date of Patent: Apr. 14, 2009

(54) DELIVERY OF THERAPEUTIC THROUGH MULTIPLE DELIVERY MEMBERS

(75) Inventors: Toby Freyman, Waltham, MA (US); Maria Palasis, Wellesley, MA (US); Wendy Naimark, Cambridge, MA (US); William J. Shaw, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 826 days.

(21) Appl. No.: 11/038,241

(22) Filed: Jan. 21, 2005

(65) Prior Publication Data

US 2006/0195059 A1    Aug. 31, 2006

(51) Int. Cl.
*A61M 25/00* (2006.01)
*A61M 29/00* (2006.01)

(52) U.S. Cl. .................... 604/264; 604/96.01
(58) Field of Classification Search ............ 604/529, 604/264, 164.01–164.13, 96.01, 272–274, 604/103
See application file for complete search history.

(56) References Cited

U.S. PATENT DOCUMENTS

| | | |
|---|---|---|
| 5,236,424 A | 8/1993 | Imran |
| 5,254,089 A | 10/1993 | Wang |
| 5,419,777 A | 5/1995 | Hofling |
| 5,457,041 A | 10/1995 | Ginaven et al. |
| 5,464,395 A | 11/1995 | Faxon et al. |
| 5,693,029 A | 12/1997 | Leonhardt |
| 5,697,901 A | 12/1997 | Eriksson |
| 5,843,033 A | 12/1998 | Ropiak |
| 5,882,332 A | 3/1999 | Wijay |
| 6,004,295 A | 12/1999 | Langer et al. |
| 6,048,332 A | 4/2000 | Duffy et al. |
| 6,063,082 A | 5/2000 | DeVore et al. |
| 6,102,904 A | 8/2000 | Vigil et al. |
| 6,217,554 B1 * | 4/2001 | Green ................ 604/164.01 |
| 6,283,951 B1 * | 9/2001 | Flaherty et al. ............ 604/529 |
| 6,302,870 B1 | 10/2001 | Jacobsen et al. |
| 6,319,230 B1 | 11/2001 | Palasis et al. |
| 6,400,980 B1 | 6/2002 | Lemelson |
| 6,620,139 B1 | 9/2003 | Plicchi |
| 2001/0049500 A1 | 12/2001 | Vantassel et al. |
| 2002/0013615 A1 | 1/2002 | Haim et al. |
| 2004/0064093 A1 | 4/2004 | Hektner et al. |

FOREIGN PATENT DOCUMENTS

| | | |
|---|---|---|
| WO | WO 01/36029 A | 5/2001 |
| WO | WO 2004/020032 A | 3/2004 |

\* cited by examiner

*Primary Examiner*—Matthew F Desanto
(74) *Attorney, Agent, or Firm*—Vidas, Arrett & Steinkraus (57) ABSTRACT

Embodiments of the present invention regard the delivery of therapeutic. One such apparatus may comprise multiple, independently-activated, injection devices for the delivery of therapeutic or other substances. This apparatus may include a first catheter; a second catheter in the first catheter and a multiple delivery member injection device. This multiple delivery member may include an expandable member and a plurality of injection elements. A third catheter may be positioned in the second catheter. This third catheter may have a distal end connected to a wall of the expandable member and a plurality of filling tubes connected to an distal end of the third catheter. In some of the embodiments each of the injection elements may hold a pressurized therapeutic prior to release of the therapeutic.

35 Claims, 9 Drawing Sheets

FIG. 21

DELIVERY OF THERAPEUTIC THROUGH MULTIPLE DELIVERY MEMBERS

FIELD OF THE INVENTION

Embodiments of the present invention relate to the delivery of therapeutic at a target site of a patient. More particularly, embodiments of the present invention relate to a system, method, and apparatus that employ multiple injection or piercing members for the delivery of therapeutic to a target site within the body of a patient.

BACKGROUND

Medical catheters are used for innumerable minimally invasive medical procedures. Catheters may be used for delivery of therapeutic drug doses to target tissue and/or for delivery of medical devices such as lumen-reinforcing or drug-eluting stents. Likewise, catheters may be used to guide medical instruments to a target site to perform a surgical procedure, such as tissue rescission, ablation of obstructive deposits or myocardial revascularization.

Myocardial injection devices may be used to deliver therapeutics to the myocardial wall to stimulate myocardial angiogenesis and myocardial tissue regeneration. Unfortunately, not all patients have ventricular walls of equal thickness, which makes it difficult to treat those patients with thin ventricular walls with a needle having a single depth. For example, if the depth of injection of the needle causes the needle tip to extend through the ventricular wall, the therapeutic will not be delivered to the desired location, and thus the effectiveness of the procedure will be compromised. Similarly, there is a wide range of wall thicknesses even within a single patient's heart, which requires multiple needles, each with a different depth of injection. In addition, large tissue areas may also need to be treated that would require numerous injections be delivered by the needle to cover the entire area. To do this, the needle would have to be positioned over and inserted into each injection site, which is time consuming and does not lend itself to an even or organized pattern of delivery of the therapeutic agent. As a result, procedural times and costs are increased due to using and switching between multiple needles and/or having to move the needle to and inject into multiple positions within the target tissue area.

BRIEF DESCRIPTION OF THE DRAWINGS

The foregoing and further features and advantages of the invention will become apparent from the following description of preferred embodiments with reference to the accompanying drawings, wherein like numerals are used to represent like elements and wherein.

DETAILED DESCRIPTION

The invention is directed to improved injection devices with multiple delivery members, and related methods of use. In certain embodiments, a device and method are provided for injecting therapeutic and other agents or fluids into a target site within a patient's body. The device may include an injection device including a first catheter and a second catheter disposed in the first catheter. The device may also include a multiple delivery member injection device including an expandable member having a proximal wall, an opposing distal wall and a circumferential side wall connecting the proximal wall and the opposing distal wall. A plurality of injection elements may be connected to the distal wall of the expandable member and an outer surface of the proximal wall of the expandable member may be connected to a distal end of the second catheter to form a liquid tight seal. The expandable member may be expandable to receive and hold a liquid under a positive pressure. The device may further include a third catheter disposed in the second catheter with a distal end of the third catheter being connected to the proximal wall of the expandable member. The device may still further include a plurality of filling tubes connected at their proximal ends. The plurality of filling tubes may provide therapeutic from the third catheter to a plurality of injection elements to produce a positive pressure in the plurality of injection elements wherein each of the plurality of injection elements may hold the pressurized therapeutic until it is released.

Some embodiments of the present invention may include a multiple delivery member injection device that may be used with catheters, for example, a Stiletto catheter manufactured by Boston Scientific of Natick, Mass. Likewise, embodiments of the present invention may also be used with catheters both with and without hoods, with and without an electrode sensor tip, and combinations of the above-described features in catheters with and without deflectable tips.

In accordance with an embodiment of the present invention, a multiple delivery member injection device may include a body with multiple small tips spaced over an exterior of the body. The multiple delivery member injection device may permit the simultaneous deployment of therapeutic agents over a tissue area without having to move, for example, roll, or lift move and replace the device over the area. This is especially useful when an area of tissue needs to be dosed with the therapeutic agent while the multiple delivery member injection device is positioned inside a patient's body, which may reduce procedural time and costs due to the tissue area that may be quickly treated with embodiments of the present invention.

In accordance with some embodiments of the present invention, each of the multiple small tips may include a reservoir, a unit to penetrate tissue, and a valve or other mechanism to control the release of the therapeutic. The reservoir may hold the therapeutic in a pressurized state so that it may be forced into the tissue when it is released. In addition, the multiple small tips may be arranged on a larger balloon, which, when inflated (i.e., pressurized), may forces the multiple small tips into contact with an inner surface of a heart, for example, an inner surface of a left ventricle. When the multiple small tips contact the inner wall they are designed to penetrate the tissue and release the therapeutic. Benefits of these and other embodiments may include minimizing trauma by using multiple small delivery sites; increased therapeutic retention due to small volumes delivered; reduced loss of agent due to insufficient purchase with tissue by release only when the capsule may be in contact with tissue; improved distribution from many evenly spaced delivery sites; minimize possibility of double-dosing the same area; and simplify delivery procedure through multiple simultaneous dosings.

While multiple embodiments are presented herein these embodiments are not limiting. The present invention may comprise these as well as other embodiments including: those that transpose, replace, substitute and remove method steps; and those that reflect the devices shown herein as well as devices that exchange components between embodiments and those that made additions or deletions in the embodiments themselves.

Figure 1:
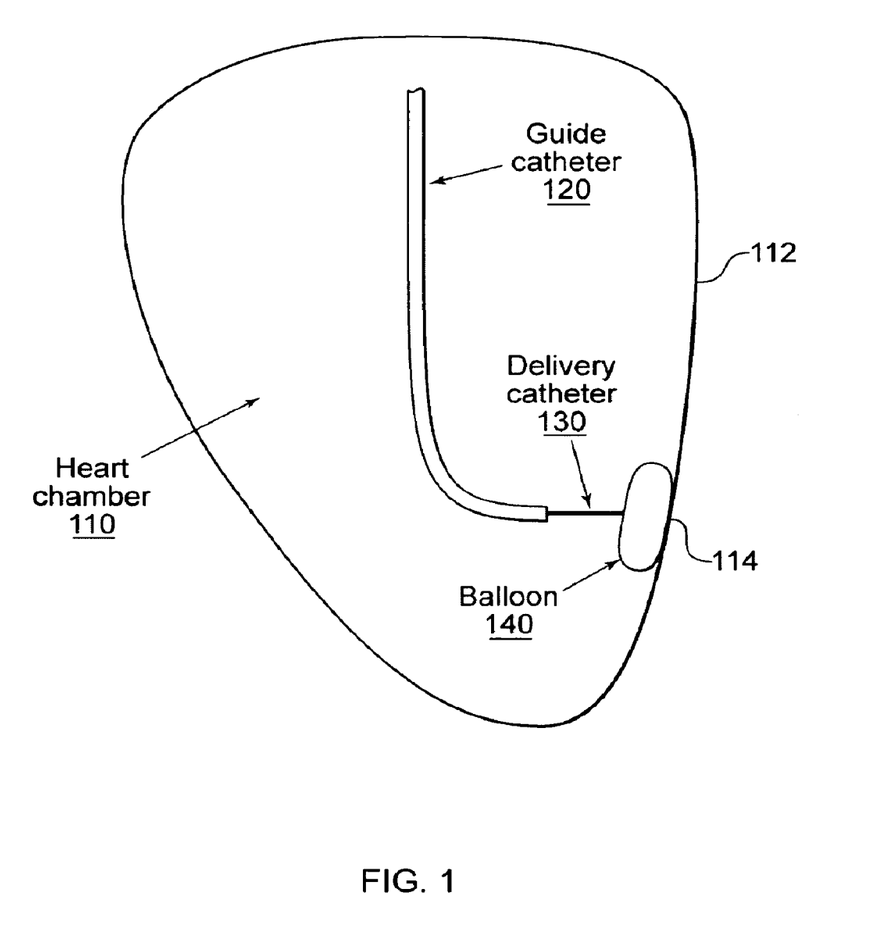
FIG. 1 is a diagrammatic cross-sectional view of a heart chamber with a catheter system and a multiple delivery member injection device inserted therein, in accordance with an embodiment of the present invention.

FIG. 1 is a diagrammatic cross-sectional view of a heart chamber with a catheter system and a multiple delivery member injection device inserted therein, in accordance with an embodiment of the present invention. In FIG. 1, a heart chamber 110 may have an inner wall 112 and inserted in heart chamber 110 may be a guide catheter 120 with a delivery catheter 130 running from a proximal end to a distal end of a lumen in guide catheter 120 so that guide catheter 120 points at a target tissue site 114 on inner wall 112. A multiple delivery member injection device 140 may be attached to a distal end of delivery catheter 130 and be placed against inner wall 112 of heart chamber 110. For example, multiple delivery member injection device 140 may include an expandable member, for example, a balloon, with multiple delivery members located on a distal surface of the expandable member. Each of the multiple delivery members may be in fluid communication with a lumen running from a proximal end to a distal end of delivery catheter 130 and inflated with a therapeutic in the lumen. For example, each of the multiple delivery members may include a one-way valve to permit the therapeutic to enter, pressure inflate and "arm" the multiple delivery member. Each multiple delivery member may also include a sharpened end, for example, a needle, to penetrate the target tissue and when the sharpened end penetrates the target tissue site to a prescribed depth, a collar within the multiple delivery member may slide back and open a valve to release the pressurized therapeutic into the target tissue. In general, a multiple delivery member may not release the pressurized therapeutic unless the collar slides back far enough to open the valve.

In FIG. 1, in accordance with embodiments of the present invention, guide catheter 120 may be an elongate tubular member having a reinforcement member, for example, a co-braided polymer tube, a co-extruded tube with two or more polymers, one or more rigid polymer or metallic wires or rods embedded in a polymer tube and two coaxial tubes, one being of a generally rigid nature mechanically joined by, for example, a heat shrink tube over a polymer tube.

In FIG. 1, in accordance with embodiments of the present invention, delivery catheter 120 may be made of various metallic and non-metallic hypodermic tubing materials. For example, metallic hypodermic tubing materials may include, but are not limited to, stainless steel and nickel-titanium alloy.

Likewise, examples of non-metallic hypodermic tubing materials may include, but are not limited to, polycarbonate, poly(L-lactide) (PLLA), poly(D,L-lactide) (PLA), polyglycolide (PGA), poly(L-lactide-co-D, L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polyhydroxybutyrate (PHBT), poly(phosphazene), polyD,L-lactide-co-caprolactone) (PLA/PCL), poly(glycolide-co-caprolactone) (PGA/PCL), polyanhydrides (PAN), poly(ortho esters), poly(phosphate ester) poly(amino acid), poly(hydroxy butyrate), polyacrylate, polyacrylamid, poly(hydroxyethyl methacrylate), polyurethane, polysiloxane and their copolymers, polyethylene (PE), polypropylene (PP), polyvinylchloride (PVC), polytetrafluoroethylene (PTFE), polyether block amide (PEBA), polyamide and polyimide.

A more detailed description of guide catheter 120 and methods of its use may be found in related U.S. patent application Ser. No. 09/635,083, entitled, "Catheter Shaft Assembly," which is hereby incorporated herein in its entirety, as well as in PCT publication WO 02/11808, published Feb. 12, 2002, which claims priority to U.S. patent application Ser. No. 09/635,083.

Figure 2:
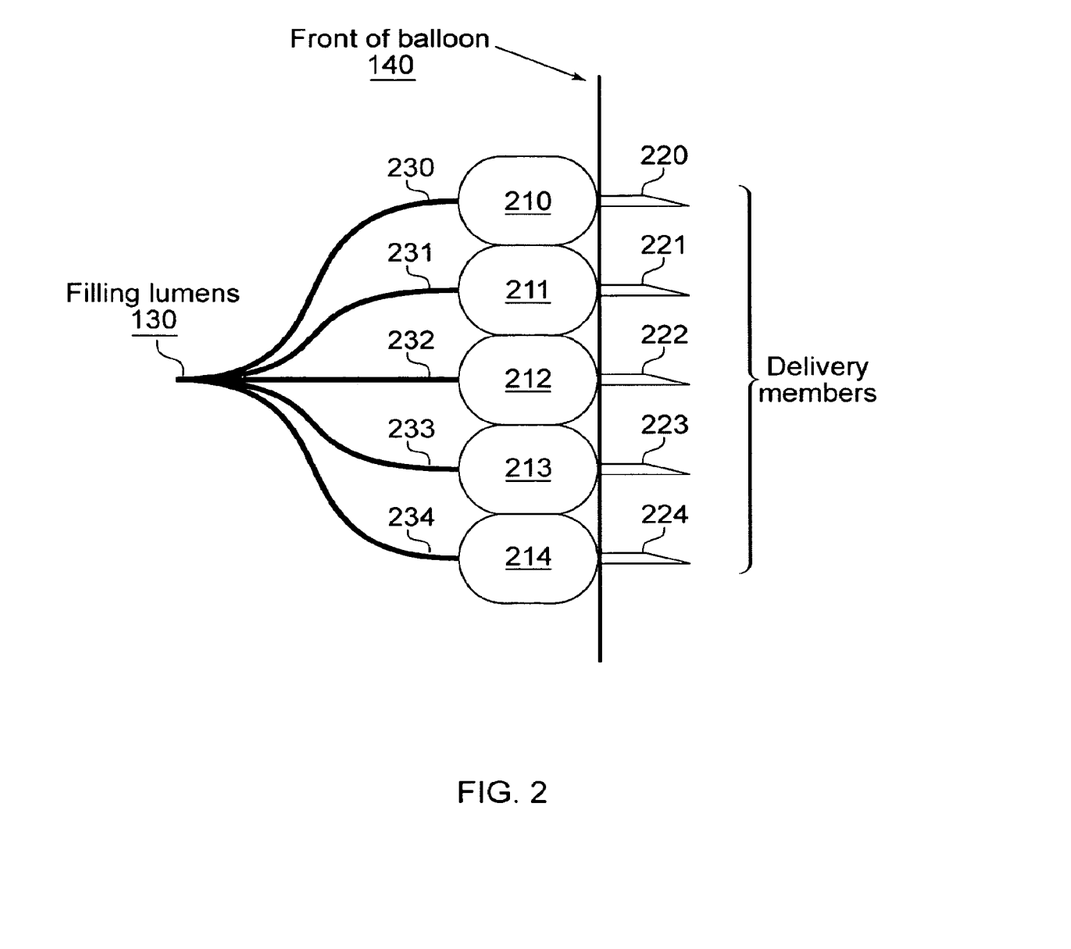
FIG. 2 is an exploded cross-sectional side view of a portion of a distal end of a multiple delivery member injection device, in accordance with an embodiment of the present invention.

FIG. 2 is an exploded cross-sectional side view of a portion of a distal end of a multiple delivery member injection device, in accordance with an embodiment of the present invention. In FIG. 2, multiple small, pressurizable capsules (i.e., reservoirs) 210 to 214 may each be connected to a needle tip 220 to 224. Each small tip may be positioned against an interior surface of expandable member 140 and the connected needle tip may extend through inner wall 112. In general, expandable member 140 may be inflated with saline that may be provided through the lumen in delivery catheter 130. For example, either through the lumen in delivery catheter 130 or a separate saline filling lumen passing therethrough. Likewise, each of the multiple small, pressurizable capsules 210 to 214 may be connected and in fluid communication with the lumen of delivery catheter 130 by filling lumens 230 to 234, respectfully.

Figure 3:
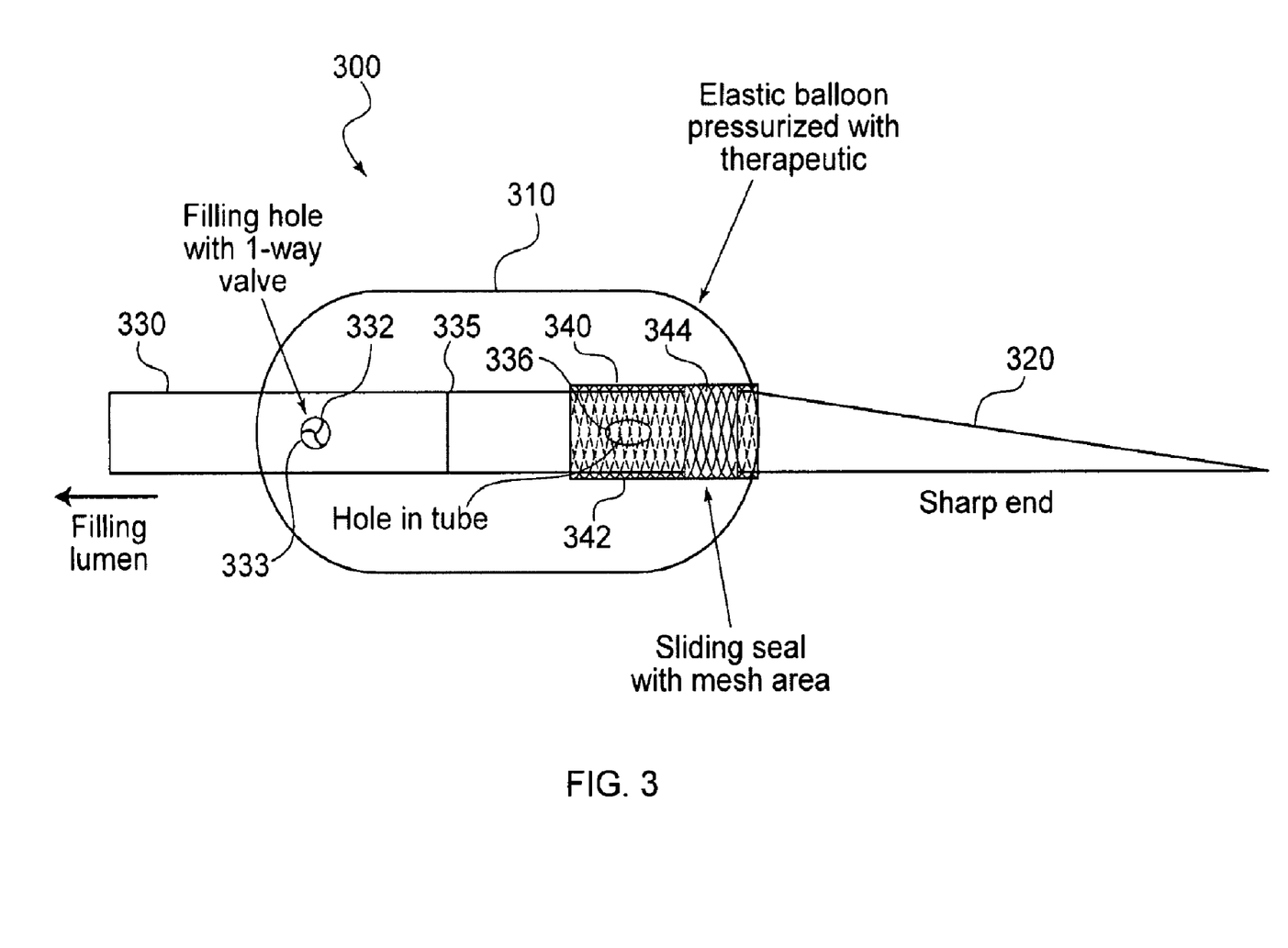
FIG. 3 is an enlarged cross-sectional side view of a single delivery member, in accordance with an embodiment of the present invention.

FIG. 3 is an enlarged cross-sectional side view of a single delivery member, in accordance with an embodiment of the present invention. In FIG. 3, a single delivery member 300 may include a pressurizable capsule 310 that may surround part of a needle tip 320 at a distal end of pressurizable capsule 310 and surround part of a filling lumen 330 at a proximal end of pressurizable capsule 310. Filling lumen 330 may include a filling hole 332 located on filling lumen within pressurizable capsule 310 to permit a liquid therapeutic from filling lumen 330 to pass into and fill pressurizable capsule 310. Filling lumen 330 may also include a seal 335 located within filling lumen 330 distally of filling hole 332 to prevent the therapeutic from flowing directly from filling lumen 330 to needle tip 320. Filling hole 332 may include a one-way valve 333 that may permit the therapeutic to flow out of filling lumen 330 into pressurizable capsule 310, but prevents the backflow of the therapeutic into filling lumen 330. Pressurizable capsule 310 may include an expandable material, for example an elastic balloon, that may expand as the therapeutic is introduced into pressurizable capsule 310 to pressurize pressurizable capsule 310. Filling lumen 330 may also include an exit hole 336 to permit the pressurized therapeutic to escape from pressurizable capsule 310 into and out of needle tip 320.

In FIG. 3, in accordance with the current embodiment, single delivery member 300 may also include a sliding seal 340 that may encircle, seal and be slidingly engaged with filling lumen 330 and be located interiorly of pressurizable capsule 310. Sliding seal 340 may be connected to an inner surface 312 of pressurizable capsule 310 to form a seal there between to prevent therapeutic to leak out of pressurizable capsule 310. Sliding seal 340 may include a seal portion 342 at a proximal end that may be of a size to cover and seal exit hole 336. Sliding seal 340 may also include a porous mesh area 344 at a distal end that when sliding seal 340 is moved proximally may move over exit hole 336 to permit the therapeutic in pressurizable capsule 310 to move through porous mesh area 344, into exit hole 336 and out needle tip 320. In general, sliding seal 340 may be moved distally and proximally by inserting needle tip 320 into and pressing the distal end of pressurizable capsule 310 against a target tissue site. A normal resting position of sliding seal 340 may be where seal portion 342 may cover and seal exit hole 336.

Alternative means and methods of releasing the therapeutic agent are contemplated and may include, for example, when each pressurizable capsule contacts a target tissue site a change in electrical potential may be caused with respect to a common ground and the change may trigger a circuit to generate pressure to release the therapeutic agent. Alternatively, the change in electrical potential may stimulate an electroactive material, for example, an electroactive polymer or piezoelectric crystal, to open a valve, dissolve a cover or change shape to release the therapeutic agent. Similarly, the release of the therapeutic agent may be affected by mechanical forces resulting from contact with tissue, for example, contracting myocardium, to break a seal, plug or other obstruction to allow the therapeutic agent to flow. In addition, the pressure to force the therapeutic agent into the tissue may be caused by the action of electroactive polymers and metals, for example, piezoelectric; magneto-strictive materials, for example, cobalt alloys; a spring or elastic recovery force due to compression; and/or twisting a tube containing the therapeutic agent.

Figure 4:
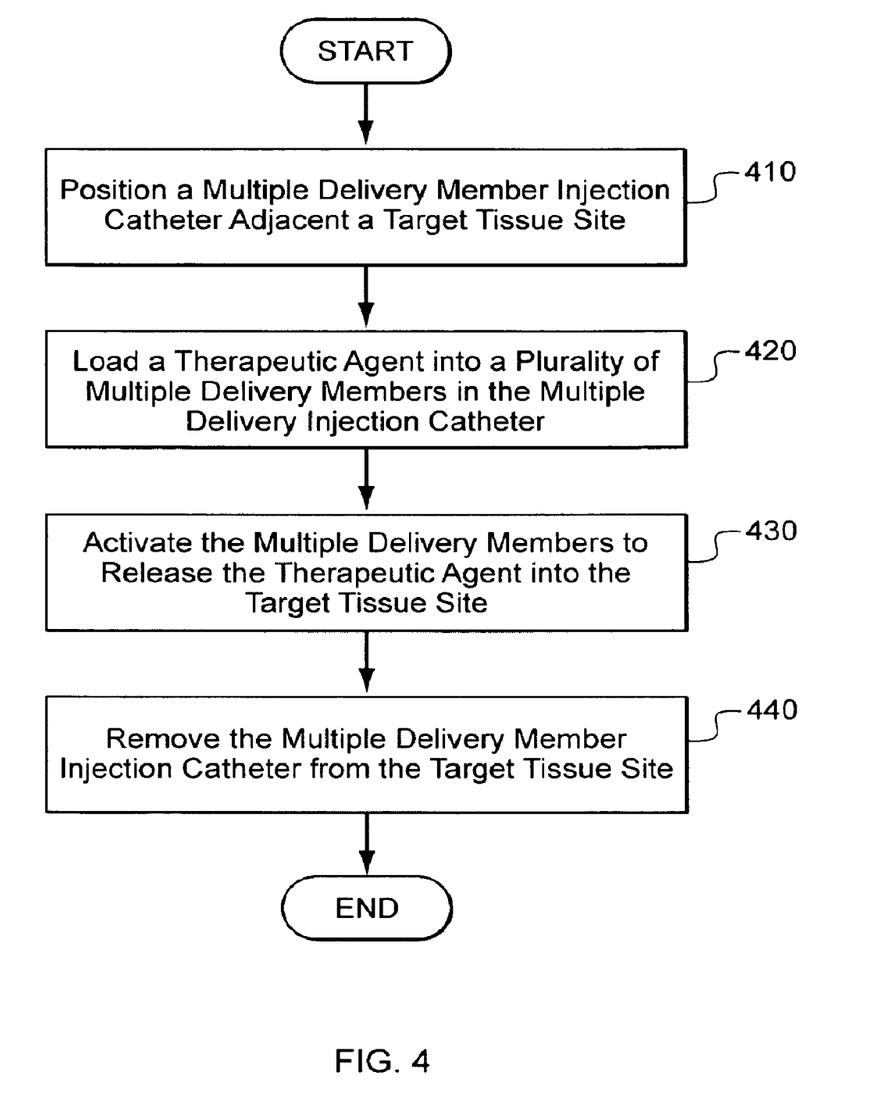
FIG. 4 is a flow diagram of a method of using a multiple delivery member injection device, in accordance with an embodiment of the present invention.

FIG. 4 is a flow diagram of a method of using a multiple delivery member injection device, in accordance with an embodiment of the present invention. In FIG. 4, the method may include positioning (410) a multiple delivery member injection catheter adjacent to a target tissue site. This may be accomplished using guide catheter 120 and delivery catheter 130 to position (410) multiple delivery member injection device 140 adjacent to the target tissue site. The method may also include loading (420) a therapeutic agent into a plurality of multiple delivery members in the multiple delivery member injection catheter. Loading (420) of the therapeutic may be accomplished by passing the therapeutic through 1-way valve 333 in filling hole 332 and into multiple delivery member injection device 140. The method may further include activating (430) the multiple delivery members to release the therapeutic agent into the target tissue site. For example, the activating (430) may be accomplished by pressing the distal end of multiple delivery member injection device 140 against the target tissue site to open exit hole 336 in each filling lumen 330 of multiple delivery member injection device 140. The method may still further include removing (440) the multiple delivery member injection catheter from the target tissue site by removing (140) multiple delivery member injection device 140, delivery catheter 130 and guide catheter 140.

Figure 5:
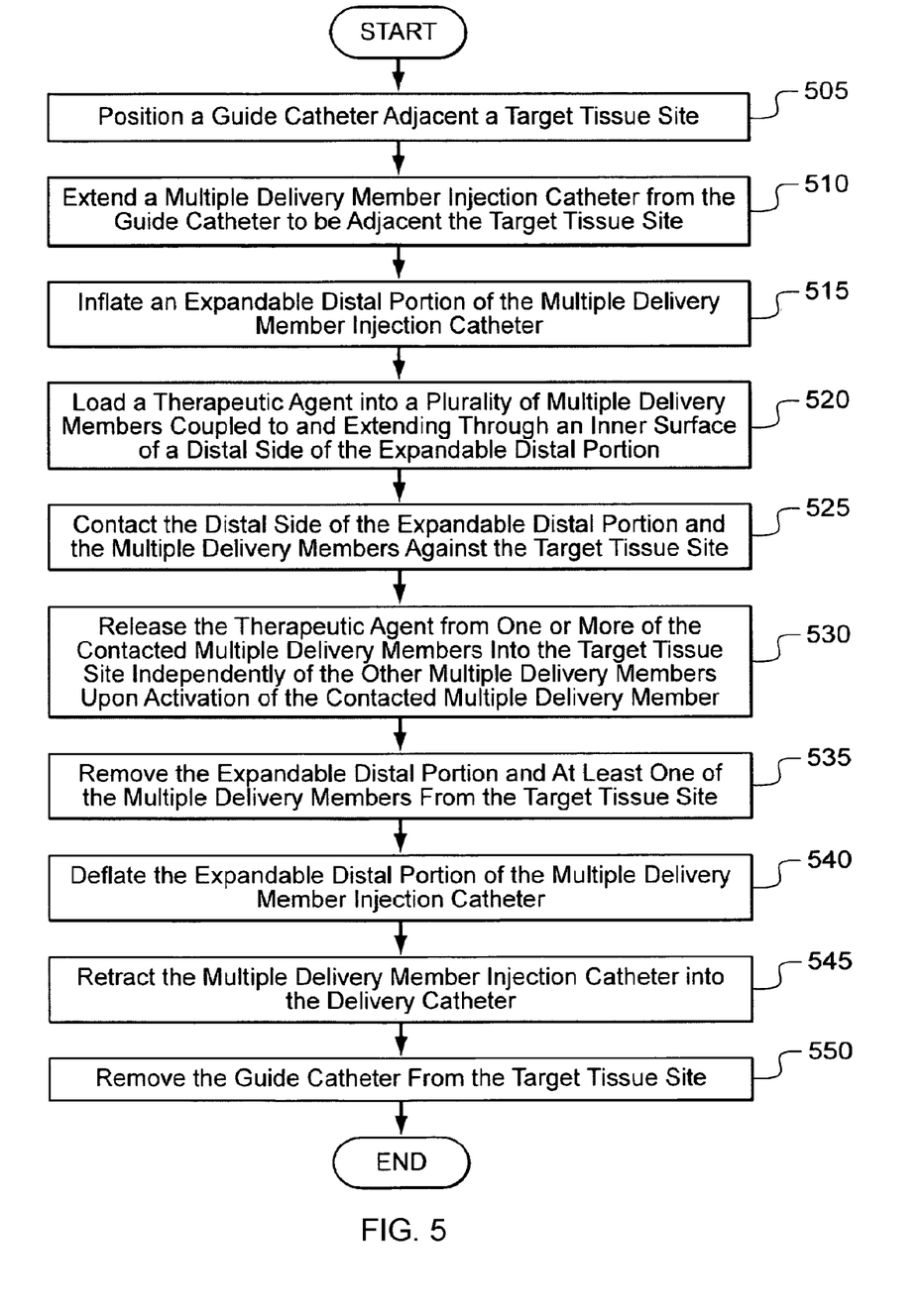
FIG. 5 is a detailed flow diagram of a method of using a multiple delivery member injection device, in accordance with an embodiment of the present invention.

FIG. 5 is a detailed flow diagram of a method of using a multiple delivery member injection device, in accordance with an embodiment of the present invention. In FIG. 5, the method may include positioning (505) a guide catheter adjacent to a target tissue site. This may be accomplished by moving guide catheter 120 through a patient's body to be adjacent to the target tissue site. The method may also include extending (510) a multiple delivery member injection catheter through the lumen and out the distal end of guide catheter 120 to be adjacent the target tissue site. The method may also include inflating (515) an expandable distal portion of the multiple delivery member injection catheter by, for example, injecting a non-therapeutic liquid, such as, a saline solution, through the lumen of delivery catheter 130 to inflate (515) the expandable distal portion. The method may further include loading (520) a therapeutic agent into a plurality of multiple delivery members coupled to and extending through an inner surface of a distal side of the expandable distal portion. For example, the therapeutic agent may be loaded (520) into multiple small, pressurizable capsules 210 to 214 through filling lumens 230 to 234.

In FIG. 5, in accordance with the present embodiment, the method may further include contacting (55) the distal side of the expandable distal portion, for example, multiple delivery member injection device 140, and the multiple delivery members, for example, multiple small, pressurizable capsules 210 to 214, against the target tissue site. The method may further include releasing (530) the therapeutic agent from one or more of the plurality of contacted multiple delivery members, for example, multiple small, pressurizable capsules 210 to 214, into the target tissue site independently of the other multiple delivery members upon activation of the contacted multiple delivery member. The method may still further include removing (535) the expandable distal portion and the multiple delivery members, for example, multiple small, pressurizable capsules 210 to 214, from the target tissue site. The method may still further include deflating (540) the expandable distal portion, for example, multiple delivery member injection device 140, of the multiple delivery member injection catheter. The method may still further include retracting (545) the multiple delivery member injection catheter, for example, multiple delivery member injection device 140, into the guide catheter, for example, delivery guide 120. The method may further still include removing (550) guide catheter 120 from the target tissue site.

Figure 6:
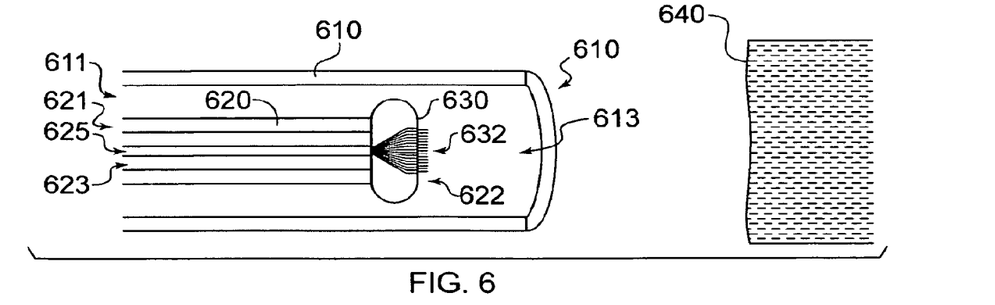
FIG. 6 is a cross-sectional side view of a portion of a distal end of a multiple delivery member injection device and a distal end of a catheter, in accordance with an embodiment of the present invention.

FIG. 6 is a cross-sectional side view of a portion of a distal end of a multiple delivery member injection device and a distal end of a catheter, in accordance with an embodiment of the present invention. In FIG. 6, a multiple delivery member injection device 600 may include a guide catheter 610, which may include a guide catheter proximal end 611, a guide catheter distal end 612 and a guide catheter lumen 613 extending there between. A delivery catheter 620 may include a delivery catheter proximal end 621, a delivery catheter distal end 622 and a delivery catheter lumen 623 extending there between. Delivery catheter 620 may also include a therapeutic delivery lumen 625 that may extend through delivery catheter lumen 623 from delivery catheter proximal end 621 to delivery catheter distal end 622. Therapeutic delivery lumen 625 and delivery catheter 620 may be connected to a proximal end of a multiple delivery member injection device 630, which may include multiple delivery members 632 located on a distal side of multiple delivery member injection device 630. In FIG. 6, multiple delivery member injection device 600 may be positioned adjacent to a target tissue site 640.

Figure 7:
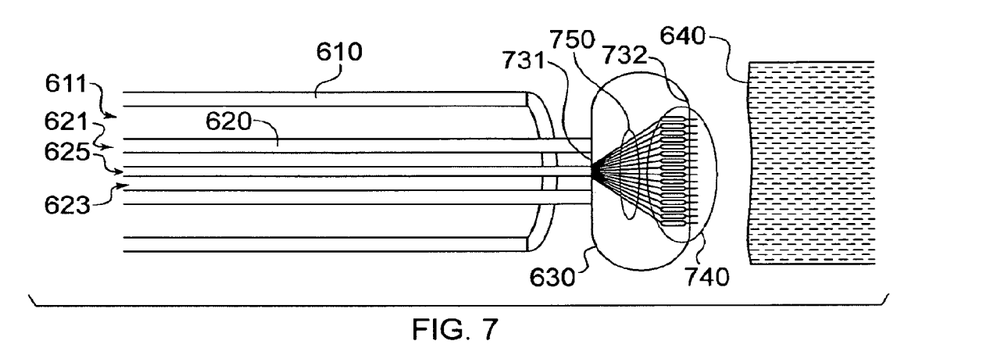
FIG. 7 is a cross-sectional side view of the portion of the distal end of the multiple delivery member injection device of FIG. 6 being shown extended past the distal end of the catheter and filled with a therapeutic, in accordance with an embodiment of the present invention.

FIG. 7 is a cross-sectional side view of the portion of the distal end of the multiple delivery member injection device of FIG. 6 being shown extended past the distal end of the catheter and filled with a therapeutic, in accordance with an embodiment of the present invention. In FIG. 7, delivery catheter 620 and multiple delivery member injection device 630 may be extended past distal end of guide catheter 611. Multiple delivery member injection device 630 may be expanded by passing a non-therapeutic liquid, for example, saline or another physiologically compatible liquid, down guide catheter lumen 613 and through an opening 731 in the proximal side of multiple delivery member injection device 630. Multiple delivery member injection device 630 may include multiple delivery members 740 that may each be connected to one of a multiple of filling lumens 750 and in fluid communication with therapeutic delivery lumen 625 through filling lumens 750. As seen in FIG. 7, multiple delivery members 740 are expanded and filled with a therapeutic supplied from therapeutic delivery lumen 625 through filling lumens 625. In FIG. 7, multiple delivery member injection device 630 is shown positioned adjacent to tissue target site 640 in a fully loaded (i.e., each of multiple delivery members 740 are pressurized with therapeutic) and ready for injection into target tissue site 640.

In FIG. 7, in some alternative embodiments of the present invention, an additional non-therapeutic delivery lumen (not shown) may be positioned in parallel with therapeutic delivery lumen and a distal end of the non-therapeutic delivery lumen may be coupled with opening 731 to permit the filling of multiple delivery member injection device 630 with a non-therapeutic.

Figure 8:
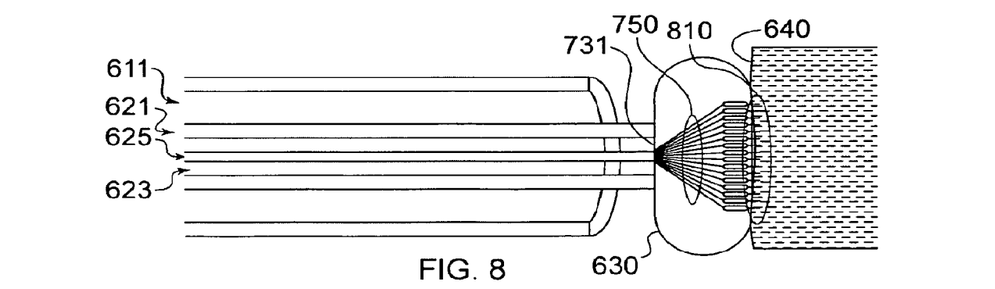
FIG. 8 is a cross-sectional side view of the portion of the distal ends of the multiple delivery member injection device and catheter of FIG. 7 with the distal end of the multiple delivery member injection device against a target tissue site, in accordance with an embodiment of the present invention.

FIG. 8 is a cross-sectional side view of the portion of the distal ends of the multiple delivery member injection device and catheter of FIG. 7 with the distal end of the multiple delivery member injection device against a target tissue site, in accordance with an embodiment of the present invention. In FIG. 8, multiple delivery member injection device 630 is shown positioned immediately against and with multiple needle tips 810 inserted into target tissue site 640, but before any of multiple delivery members 740 has been activated to release its therapeutic into target tissue site 640.

Figure 9:
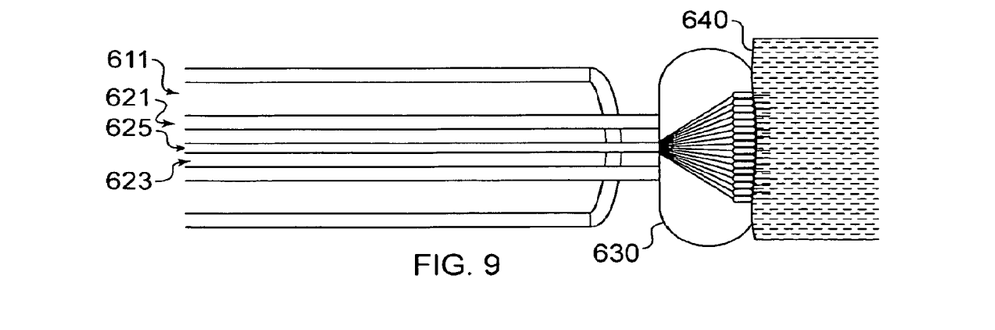
FIG. 9 is a cross-sectional side view of the portion of the distal ends of the multiple delivery member injection device and catheter of FIG. 8 after the multiple delivery member injection device has injected the therapeutic into the target tissue site, in accordance with an embodiment of the present invention.

FIG. 9 is a cross-sectional side view of the portion of the distal ends of the multiple delivery member injection device and catheter of FIG. 8 after the multiple delivery member injection device has injected the therapeutic into the target tissue site, in accordance with an embodiment of the present invention. In FIG. 9, multiple delivery member injection device 630 is shown positioned pressed against target tissue site 640 with each of multiple delivery members 740 having been activated to release its therapeutic into target tissue site 640.

Figure 10:
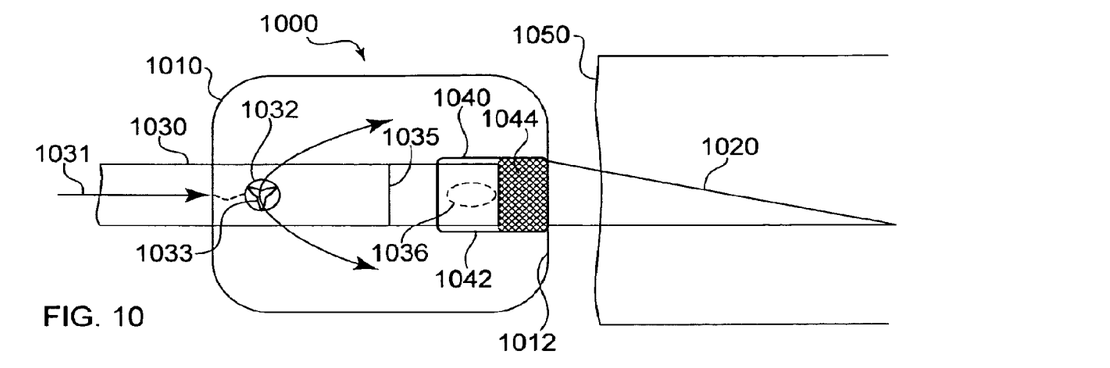
FIG. 10 is a cross-sectional side view of a single delivery member injection device that is similar to the device in FIG. 3 with a needle and a body fully expanded and filled with a therapeutic where the needle is partially inserted into a target tissue site to deliver the therapeutic, in accordance with another embodiment of the present invention.

FIG. 10 is a cross-sectional side view of a single delivery member injection device that is similar to the device in FIG. 3 with a needle and a body fully expanded and filled with a therapeutic where the needle is partially inserted into a target tissue site to deliver the therapeutic, in accordance with another embodiment of the present invention. In FIG. 10, a single delivery member injection device 1000 may include a pressurizable capsule 1010 that may surround part of a needle tip 1020 at a distal end of pressurizable capsule 1010 and surround part of a filling lumen 1030 at a proximal end of pressurizable capsule 1010. Filling lumen 1030 may include a filling hole 1032 located on filling lumen within pressurizable capsule 1010 to permit a liquid therapeutic 1031 from filling lumen 1030 to pass into, fill and positively pressurize pressurizable capsule 1010. Filling lumen 1030 may also include a seal 1035 located within filling lumen 1030 distally of filling hole 1032 to prevent the therapeutic from flowing directly from filling lumen 1030 to needle tip 1020. Filling hole 1032 may include a one-way valve 1033 to permit therapeutic liquid 1031 to flow out of filling lumen 1030 into pressurizable capsule 1010, but prevent the backflow of therapeutic liquid 1031 into filling lumen 1030. Pressurizable capsule 1010 may include an expandable material, for example an elastic balloon, that may expand as therapeutic liquid 1031 is introduced into pressurizable capsule 1010 to pressurize pressurizable capsule 1010. Filling lumen 1030 may also include an exit hole 1036 to permit the pressurized therapeutic liquid 1031 to escape from pressurizable capsule 1010 into and out of needle tip 1020.

In FIG. 10, in accordance with the current embodiment, single delivery member 1000 may also include a sliding seal 1040 that may encircle, seal and be slidingly engaged with filling lumen 1030 and be located interiorly of pressurizable capsule 1010. Sliding seal 1040 may be connected to an inner surface 1012 of pressurizable capsule 1010 to form a seal there between to prevent therapeutic liquid 1031 from leaking out of pressurizable capsule 1010. Sliding seal 1040 may include a seal portion 1042 at a proximal end that may be of a size to cover and seal exit hole 1036. Sliding seal 1040 may also include a porous mesh area 1044 at the distal end that when sliding seal 1040 is moved proximally may move over exit hole 1036 to permit therapeutic liquid 1031 in pressurizable capsule 1010 to move through porous mesh area 1044, into exit hole 1036 and out needle tip 1020. In general, sliding seal 1040 may be moved distally and proximally by inserting needle tip 1020 into and pressing the distal end of pressurizable capsule 1010 against a target tissue site 1050. A normal resting position of sliding seal 1040 may be where seal portion 1042 may cover and form a liquid-tight seal over exit hole 1036.

In FIG. 10, in accordance with the present embodiment, single delivery member injection device 1000 may be seen positioned adjacent target tissue site 1050 with needle 1020 partly inserted into target tissue site 1050, but before being activated to release therapeutic liquid 1031 contained in single delivery member injection device 1000.

Figure 11:
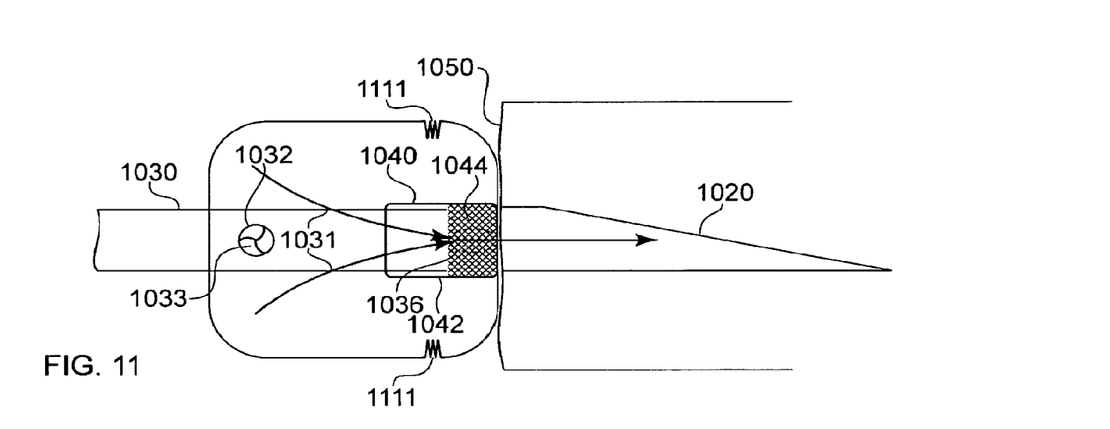
FIG. 11 is a cross-sectional side view of the single delivery member injection device of FIG. 10 with the body of the device partially retracted and pressed against and the needle fully inserted into the target tissue site to permit the therapeutic to be delivered to the target tissue site, in accordance with an embodiment of the present invention.

FIG. 11 is a cross-sectional side view of the single delivery member injection device of FIG. 10 with the body of the device partially retracted and pressed against and the needle fully inserted into the target tissue site to permit the therapeutic to be delivered to the target tissue site, in accordance with an embodiment of the present invention. In FIG. 11, the distal end of pressurizable capsule 1010 is shown in a compressed position with folds 1111 and pressed against target tissue site 1050 with sliding seal 1040 moved proximally so that mesh area 1044 is over exit hole 1036 and therapeutic liquid 1031 is escaping through exit hole 1036 and out of needle tip 1020 into target tissue site 1050. As soon as mesh area 1044 uncovers exit hole 1036 to permit therapeutic liquid 1031 to be ejected, the positive pressure in pressurizable capsule 1010 forces therapeutic liquid 1031 through exit hole 1036 and into and out of needle tip 1020.

Figure 12:
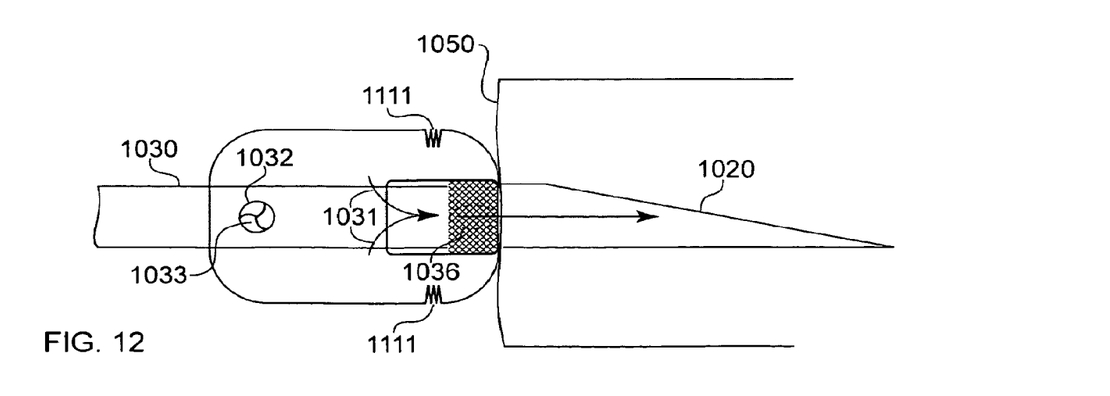
FIG. 12 is a cross-sectional side view of the single delivery member injection device of FIG. 11 with the body of the device fully retracted and pressed against and the needle fully inserted into the target tissue site, in accordance with an embodiment of the present invention.

FIG. 12 is a cross-sectional side view of the single delivery member injection device of FIG. 11 with the body of the device fully retracted and pressed against and the needle fully inserted into the target tissue site, in accordance with an embodiment of the present invention. In FIG. 12, pressurizable capsule 1010 is still in a compressed position with folds 1111 against target tissue site 1050 and sliding seal 1040 over exit hole 1036 as the last of therapeutic liquid 1031 escapes out exit hole 1036 into needle tip 1020 and target tissue 1050. Upon retracting pressurizable capsule 1010 from target tissue site, the distal end of pressurizable capsule 1010 and sliding seal 1040 may move distally to again seal exit hole with seal portion 1042 of sliding seal 1040.

In FIG. 12, alternate embodiments are contemplated in which pressurizable capsule 1010 does not have folds 1111, but upon being pressed against target tissue site 1050 the sides of pressurizable capsule 1010 may bulge out to increase the positive pressure within pressurizable capsule 1010. Upon mesh area 1044 being moved far enough in the proximal direction to uncover exit hole 1036, therapeutic 1031 may be forced out of exit hole 1036 into and out of needle tip 1020 into target tissue site 1050.

Figure 13:
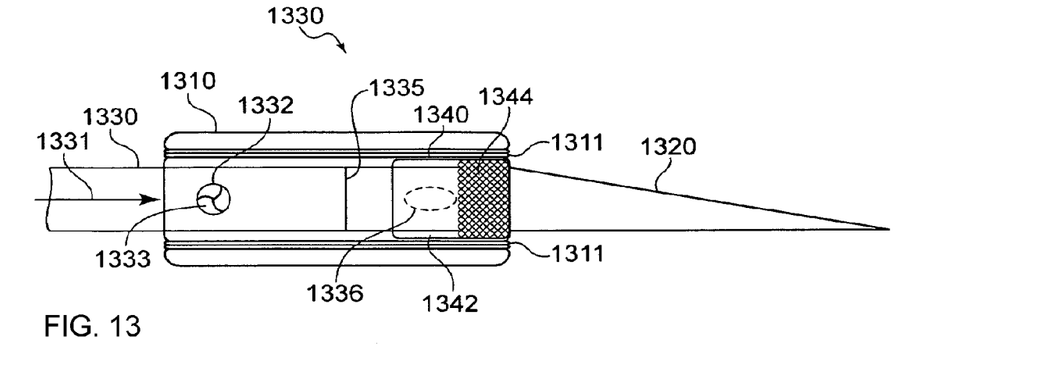
FIG. 13 is a cross-sectional side view of a single delivery member injection device with a needle and a body that is fully retracted just before it is to receive a therapeutic, in accordance with another embodiment of the present invention.

FIG. 13 is a cross-sectional side view of a single delivery member injection device with a needle and a body that is fully retracted just before it is to receive a therapeutic, in accordance with another embodiment of the present invention. In FIG. 13, a single delivery member injection device 1300 is shown in its fully retracted state ready to receive a therapeutic liquid 1331. Single delivery member injection device 1300 may include a pressurizable capsule 1310 that may surround part of a needle tip 1320 at a distal end of pressurizable capsule 1310 and surround part of a filling lumen 1330 at a proximal end of pressurizable capsule 1310. Filling lumen 1330 may include a filling hole 1332 located on filling lumen within pressurizable capsule 1310 to permit a liquid therapeutic 1331 from filling lumen 1330 to pass into, fill and positively pressurize pressurizable capsule 1310. Filling lumen 1330 may also include a seal 1335 located within filling lumen 1330 distally of filling hole 1332 to prevent the therapeutic from flowing directly from filling lumen 1330 to needle tip 1320. Filling hole 1332 may include a one-way valve 1033 to permit therapeutic liquid 1331 to flow out of filling lumen 1330 into pressurizable capsule 1310, but prevent the backflow of therapeutic liquid 1331 into filling lumen 1330. Pressurizable capsule 1310 may include an expandable material, for example an elastic balloon, that may expand as therapeutic liquid 1331 is introduced into pressurizable capsule 1310 to pressurize pressurizable capsule 1310. Pressurizable capsule 1310 may include two expandable rib sections 1311 running around pressurizable capsule 1310 and parallel to filling lumen 1330. In general, two expandable rib sections 1311 may be located on opposites sides of filling lumen 1330 to permit a substantially uniform expansion of pressurizable capsule 1310 upon introduction of therapeutic liquid 1331. Filling lumen 1330 may also include an exit hole 1336 to permit the pressurized therapeutic liquid 1331 to escape from pressurizable capsule 1310 into and out of needle tip 1320.

In FIG. 13, in accordance with the current embodiment, single delivery member 1000 may also include a sliding seal 1340 that may encircle, seal and be slidingly engaged with filling lumen 1330 and be located interiorly of pressurizable capsule 1310. Sliding seal 1340 may be connected to an inner surface 1312 of pressurizable capsule 1310 to form a seal there between to prevent therapeutic liquid 1331 from leaking out of pressurizable capsule 1310. Sliding seal 1340 may include a seal portion 1342 at a proximal end that may be of a size to cover and seal exit hole 1336. Sliding seal 1340 may also include a porous mesh area 1344 at the distal end that when sliding seal 1340 is moved proximally may move over exit hole 1336 to permit therapeutic liquid 1331 in pressurizable capsule 1310 to move through porous mesh area 1344, into exit hole 1336 and out needle tip 1320. In general, sliding seal 1340 may be moved distally and proximally by inserting needle tip 1320 into and pressing the distal end of pressurizable capsule 1310 against a target tissue site 1350. A normal resting position of sliding seal 1340 may be where seal portion 1342 may cover and form a liquid-tight seal over exit hole 1336.

Figure 14:
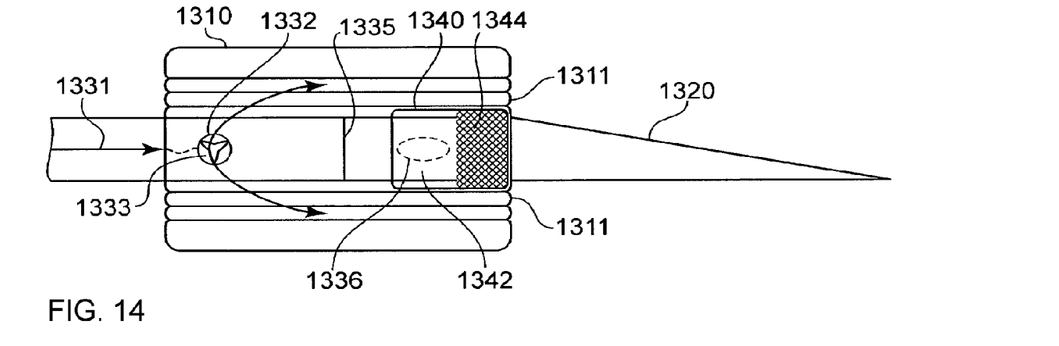
FIG. 14 is a cross-sectional side view of the single delivery member injection device of FIG. 13 with the body of the device expanded and filled with the therapeutic, in accordance with an embodiment of the present invention.

FIG. 14 is a cross-sectional side view of the single delivery member injection device of FIG. 13 with the body of the device expanded and filled with the therapeutic, in accordance with an embodiment of the present invention. In FIG. 14, therapeutic liquid 1331 has been forced through filling hole 1332 into and expanding pressurizable capsule 1310. Specifically, expandable rib sections 1311 as well as pressurizable capsule 1310 itself may be expanded to permit therapeutic liquid 1331 to be put under positive pressure within pressurizable capsule 1310.

Figure 15:
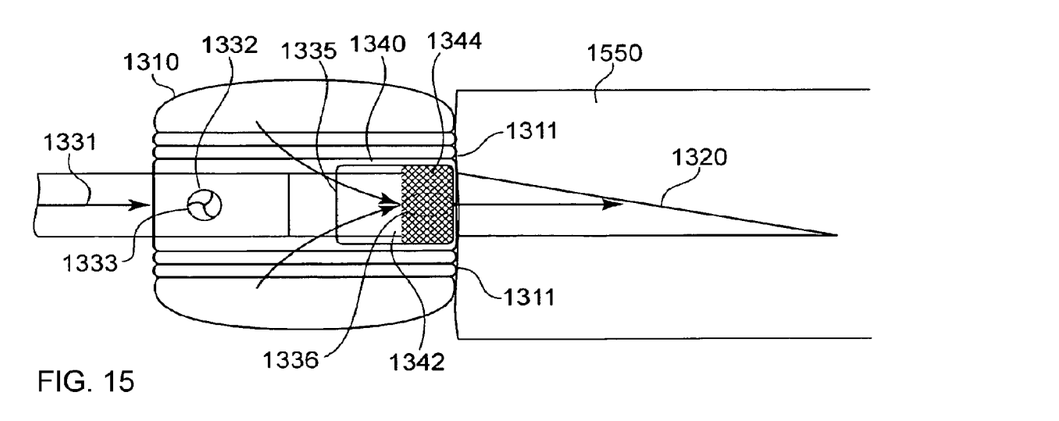
FIG. 15 is a cross-sectional side view of the single delivery member injection device of FIG. 14 with the body of the device partially retracted and pressed against and the needle fully inserted into a target tissue site to inject the therapeutic, in accordance with an embodiment of the present invention.

FIG. 15 is a cross-sectional side view of the single delivery member injection device of FIG. 14 with the body of the device partially retracted and pressed against and the needle fully inserted into a target tissue site to inject the therapeutic, in accordance with an embodiment of the present invention. In FIG. 15, the distal end of pressurizable capsule 1310 is shown in a compressed position against a target tissue site 1550 with sides of pressurizable capsule 1310 bulging outwardly. Pressurizable capsule 1310 may also have sliding seal 1340 moved proximally so that mesh area 1344 is over exit hole 1336 and therapeutic liquid 1331 is escaping through exit hole 1336 and out of needle tip 1320 into target tissue site 1550. As soon as mesh area 1344 uncovers exit hole 1336 to permit therapeutic liquid 1331 to be ejected, the positive pressure in pressurizable capsule 1310 may force therapeutic liquid 1331 through exit hole 1336 and into and out of needle tip 1320.

Figure 16:
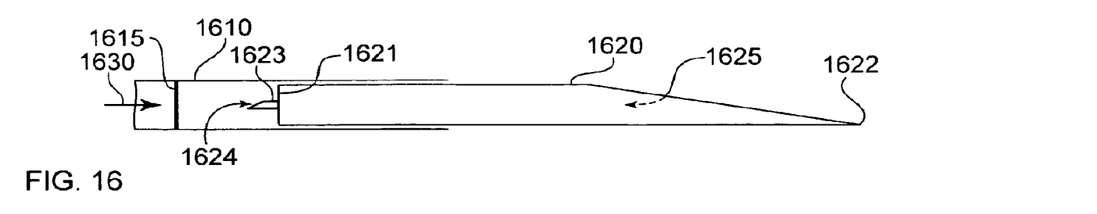
FIG. 16 is a cross-sectional side view of an alternative single delivery member injection device with a two-part needle in a closed position, in accordance with an embodiment of the present invention.

FIG. 16 is a cross-sectional side view of an alternative single delivery member injection device with a separate needle in a closed position, in accordance with an embodiment of the present invention. In FIG. 16, a two-part injection device 1600 may include a delivery catheter 1610 with a proximal end and a distal end and an inner seal 1615 disposed in delivery catheter 1610 to form a liquid-tight seal near the distal end of delivery catheter 1610. Two-part injection device 1600 may also include a needle tip 1620 slidably disposed within the distal end of delivery catheter 1610 distal of inner seal 1615. Needle tip 1620 may include a proximal end 1621 and a distal end 1622 and proximal end 1621 may include a puncture tip 1623 with a puncture tip lumen 1624 to permit fluid communication from outside proximal end 1621 into a needle tip lumen 1625 of needle tip 1620. Needle tip lumen 1625 may extend between proximal end 1621 and distal end 1622 and be open at distal end 1622 to permit the fluid to exit from needle tip 1620. In embodiments of the present invention, proximal end 1621 of needle tip 1620 and the distal end of delivery catheter 1610 may be configured to prevent needle tip 1620 from being ejected from delivery catheter 1610. For example, proximal end 1621 and the distal end of delivery catheter 1610 may each may include a stop mechanism, such as a stop ring, (not shown) to engage the other and prevent needle tip 1620 from being ejected from delivery catheter 1610.

In FIG. 16, in accordance with the present embodiment, inner seal 1615 may act as both a seal to prevent liquid in delivery catheter 1610 from passing and to prevent needle tip 1620 from moving proximally within delivery lumen past inner seal 1615. Inner seal 1615 may also include a puncturable material to permit puncture tip 1623 to penetrate inner seal 1615 and permit a therapeutic liquid 1630 to pass through puncture tip lumen 1624 and into needle tip lumen 1625, but not permit needle tip 1620 to move and/or destroy inner seal 1615.

Figure 17:
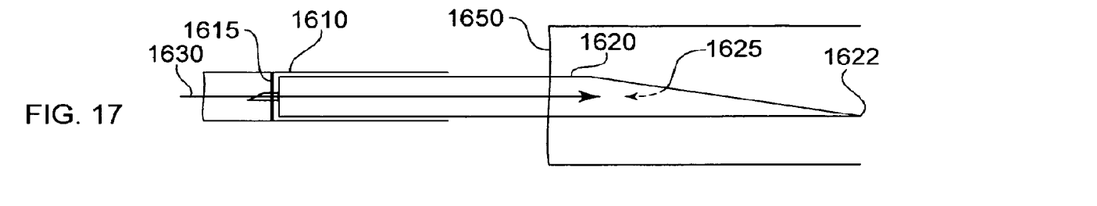
FIG. 17 is a cross-sectional side view of the alternative single delivery member injection device of FIG. 16 with the two-part needle in an open position to dispense a therapeutic, in accordance with the embodiment of the present invention.

FIG. 17 is a cross-sectional side view of the alternative single delivery member injection device of FIG. 16 with the separate needle in an open position to dispense a therapeutic, in accordance with the embodiment of the present invention. In FIG. 17, proximal end 1621 of needle tip 1620 is shown to have been moved proximally so that puncture tip 1623 has penetrated inner seal 1615 to permit therapeutic liquid 1630 to flow through puncture tip lumen 1624 and needle tip lumen 1625 and into a target tissue 1750 that needle tip 1620 has been inserted.

Embodiments of two-part injection device 1600 are contemplated in which needle tip 1620 may be either unbiased or biased away from inner seal 1615. In the unbiased embodiment, after the proximal movement of needle tip 1620 and penetration of inner seal 1615 by puncture tip 1623, needle tip 1620 may remain against inner seal 1615 when the device is removed from target tissue 1750 or may move distally due to friction between target tissue 1750 and an exterior surface of needle tip 1620 until needle tip 1620 is completely removed from target tissue 1620 and/or proximal end 1621 of needle tip 1620 and the distal end of delivery lumen 1610 engage and stop each other. In some biased embodiments, puncture tip 1623 may be removed from inner seal 1615 when needle tip 1620 is moved distally upon removal from target tissue 1750. Inner seal 1615 may include a healable material that may seal over after puncture tip 1623 is removed.

Figure 18:
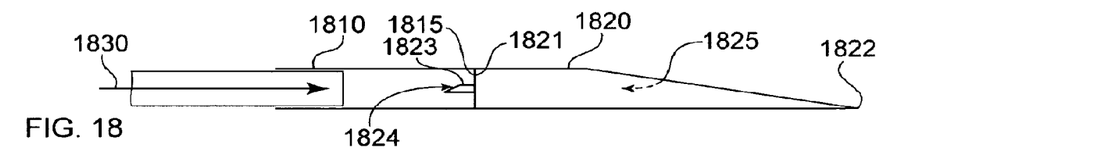
FIG. 18 is a cross-sectional side view of an alternative single delivery member injection device with a two-part needle in a closed position, in accordance with another embodiment of the present invention.

FIG. 18 is a cross-sectional side view of an alternative single delivery member injection device with a separate needle in a closed position, in accordance with another embodiment of the present invention. In FIG. 18, a two-part injection device 1800 may include a delivery catheter 1810 with a proximal end and a distal end and an end seal 1815 disposed in delivery catheter 1810 to form a liquid-tight seal at the distal end of delivery catheter 1810. Two-part injection device 1800 may also include a needle tip 1820 slidably disposed around the distal end of delivery catheter 1810. Needle tip 1820 may include a proximal end 1821 and a distal end 1822 and proximal end 1821 may include a puncture tip 1823 with a puncture tip lumen 1824 to permit fluid communication from outside proximal end 1821 into a needle tip lumen 1825 of needle tip 1820. Needle tip lumen 1825 may extend between proximal end 1821 and distal end 1822 and be open at distal end 1822 to permit the fluid to exit from needle tip 1820. In embodiments of the present invention, proximal end 1821 of needle tip 1820 and the distal end of delivery catheter 1810 may be configured to prevent needle tip 1820 from being ejected from delivery catheter 1810. For example, proximal end 1821 and the distal end of delivery catheter 1810 may each may include a stop ring (not shown) to engage the other and prevent needle tip 1820 from being ejected from delivery catheter 1810.

In FIG. 18, in accordance with the present embodiment, end seal 1815 may act as both a seal to prevent liquid in delivery catheter 1810 from passing and to prevent proximal end 1821 of needle tip 1820 from moving proximally past end seal 1815. End seal 1815 may also include a puncturable material to permit puncture tip 1823 to penetrate end seal 1815 and permit a therapeutic liquid 1830 to pass through puncture tip lumen 1824 and into needle tip lumen 1825, but not permit needle tip 1820 to move and/or destroy end seal 1815.

Figure 19:
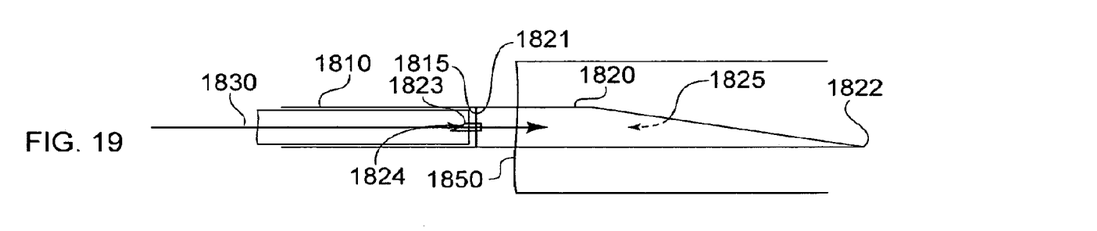
FIG. 19 is a cross-sectional side view of the alternative single delivery member injection device of FIG. 16 with the two-part needle in an open position to dispense a therapeutic, in accordance with the another embodiment of the present invention.

FIG. 19 is a cross-sectional side view of the alternative single delivery member injection device of FIG. 18 with the separate needle in an open position to dispense a therapeutic, in accordance with another embodiment of the present invention. In FIG. 19, proximal end 1821 of needle tip 1820 is shown to have been moved proximally so that puncture tip 1823 has penetrated end seal 1815 to permit therapeutic liquid 1830 to flow through puncture tip lumen 1824 and needle tip lumen 1825 and into a target tissue 1950 that needle tip 1820 has been inserted.

Embodiments of two-part injection device 1800 are contemplated in which needle tip 1820 may be either unbiased or biased away from inner seal 1815. In the unbiased embodiment, after the proximal movement of needle tip 1820 and penetration of inner seal 1815 by puncture tip 1823, needle tip 1820 may remain against inner seal 1815 when the device is removed from target tissue 1950 or may move distally due to friction between target tissue 1950 and an exterior surface of needle tip 1820 until needle tip 1820 is completely removed from target tissue 1820 and/or proximal end 1821 of needle tip 1820 and the distal end of delivery lumen 1810 engage and stop each other. In some biased embodiments, puncture tip 1823 may be removed from inner seal 1815 when needle tip 1820 is moved distally upon removal from target tissue 1950. Inner seal 1815 may include a healable material that may seal over after puncture tip 1823 is removed.

Figure 20:
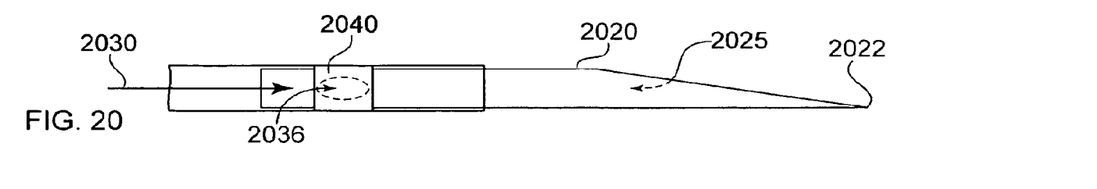
FIG. 20 is a cross-sectional side view of an alternative single delivery member injection device with a two-part needle in a closed position, in accordance with yet another embodiment of the present invention.

FIG. 20 is a partial cross-sectional side view of an alternative single delivery member injection device with a separate needle in a closed position, in accordance with yet another embodiment of the present invention. In FIG. 20, a two-part injection device 2000 may include a delivery catheter 2010 with a proximal end and a distal end and an inner band seal 2015 disposed around an inner wall of delivery catheter 2010 to form a liquid-tight seal between the inner wall of delivery catheter 2010 and an outer wall of a proximal end of a needle tip 2020. Needle tip 2020 may be slidably disposed within the distal end of delivery catheter 2010 and inner band seal 2015. Needle tip 2020 may include a proximal end 2021 and a distal end 2022 and an exit hole 2023 in the side of needle tip 2020 near proximal end 2021 to permit fluid communication from outside needle tip 2020 into a needle tip lumen 2025 of needle tip 2020. Needle tip lumen 2025 may extend between proximal end 2021 and distal end 2022 and be open at distal end 2022 to permit the fluid to exit from needle tip 2020. As shown in FIG. 20, inner band seal 2015 is shown covering and sealing exit hole 2023 in the side of needle tip 2020. In embodiments of the present invention, proximal end 2021 of needle tip 2020 and the distal end of delivery catheter 2010 may be configured to prevent needle tip 2020 from being ejected from delivery catheter 2010. For example, proximal end 2021 and the distal end of delivery catheter 2010 may each include a stop mechanism, such as a stop ring, (not shown) to engage the other and prevent needle tip 2020 from being ejected from delivery catheter 2010.

In FIG. 20, in accordance with the present embodiment, inner band seal 2015 may act to seal completely around needle tip 2020 to prevent liquid in delivery catheter 2010 from passing into needle tip 2020 even if needle tip 2020 is rotated. Alternative embodiments are also contemplated in which inner band seal 2015 may encircle only a portion of needle tip 2020 including exit hole 2023. In these embodiments exit hole 2023 may be uncovered by either moving needle tip 2020 proximally to move inner band seal 2015 off exit hole 2023 or by rotating delivery catheter 2010 to move inner band seal 2015 off exit hole 2023.

Figure 21:
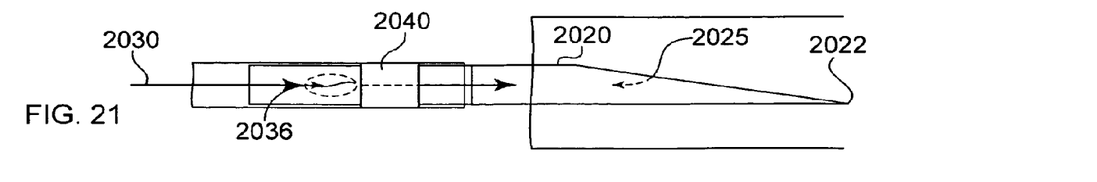
FIG. 21 is a cross-sectional side view of the alternative single delivery member injection device of FIG. 20 with the two-part needle in an open position to dispense a therapeutic, in accordance with the yet another embodiment of the present invention.

FIG. 21 is a partial cross-sectional side view of the alternative single delivery member injection device of FIG. 20 with the separate needle in an open position to dispense a therapeutic, in accordance with the yet another embodiment of the present invention. In FIG. 21, proximal end 2021 of needle tip 2020 is shown to have been moved proximally so that inner band seal 1615 has moved off of exit hole 2023 to permit therapeutic liquid 1630 to flow through exit hole 2023 into a target tissue 2150 that needle tip 2020 has been inserted.

Embodiments of two-part injection device 2000 are contemplated in which needle tip 2020 may be either unbiased or biased away from inner seal 2015. In some unbiased embodiments, after the proximal movement of needle tip 2020 and uncovering of exit hole 2023, exit hole 2023 may remain uncovered when the device is removed from target tissue 2150. Alternatively, exit hole 2023 may be partially or completely covered due to friction between target tissue 2150 and the outer wall of needle tip 2020 until needle tip 2020 is completely removed from target tissue 2020 and/or proximal end 2021 of needle tip 2020 and the distal end of delivery lumen 2010 engage and stop each other. In some biased embodiments, exit hole 2023 may be again covered by inner band seal 2015 when needle tip 2020 is moved distally upon removal from target tissue 2150.

The therapeutic agent may be any pharmaceutically acceptable agent such as a non-genetic therapeutic agent, a biomolecule, a small molecule, or cells.

Exemplary non-genetic therapeutic agents include anti-thrombogenic agents such heparin, heparin derivatives, prostaglandin (including micellar prostaglandin E1), urokinase, and PPack (dextrophenylalanine proline arginine chloromethylketone); anti-proliferative agents such as enoxaprin, angiopeptin, sirolimus (rapamycin), tacrolimus, everolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estrodiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis (2-aminoethyl)ethyleneglycol-N,N,N',N'-tetraacetic acid and mixtures thereof; antibiotics such as gentamycin, rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as lisidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promotors such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; inhibitors of heat shock proteins such as geldanamycin; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include monocyte chemoattractant proteins ("MCP-1") and bone morphogenic proteins ("BMP's"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. Preferred BMPS are any of BMP-2, BMP-3, BMP-4, BMP-5, BMP-6, and BMP-7. These BMPs can be provided as homdimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them. Non-limiting examples of genes include survival genes that protect against cell death, such as anti-apoptotic Bcl-2 family factors and Akt kinase and combinations thereof. Non-limiting examples of angiogenic factors include acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor, and insulin like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Others cells that may be used include: side populations cells, lineage negative cells, mesenchymal stem cells, cord blood cells, cardiac derived stem cells, tissue derived stem cells, bone marrow cells, endothelial progenitor cells, skeletal myoblasts, muscle derived cells, go cells, fibroblasts, smooth muscle cells, pacing cells, embryonic stem cell clones, fetal cells, neonatal cells, masked cells, tissue engineered grafts, and teratoma derived cells.

Any of the therapeutic agents may be combined to the extent such combination is biologically compatible.

Any of the above mentioned therapeutic agents may be incorporated into a polymeric coating on the medical device or applied onto a polymeric coating on a medical device. The polymers of the polymeric coatings may be biodegradable or non-biodegradable. Non-limiting examples of suitable non-biodegradable polymers include polyisobutylene copolymers and styrene-isobutylene-styrene block copolymers such as styrene-isobutylene-styrene tert-block copolymers (SIBS); polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHDROL®); squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L,-lactide), poly(lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

In a preferred embodiment, the polymer is polyacrylic acid available as HYDROPLUS® (Boston Scientific Corporation, Natick, Mass.), and described in U.S. Pat. No. 5,091,205, the disclosure of which is incorporated by reference herein. In a more preferred embodiment, the polymer is a co-polymer of polylactic acid and polycaprolactone.

Such coatings used with the present invention may be formed by any method known to one in the art. For example, an initial polymer/solvent mixture can be formed and then the therapeutic agent added to the polymer/solvent mixture. Alternatively, the polymer, solvent, and therapeutic agent can be added simultaneously to form the mixture. The polymer/solvent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coating may comprise multiple polymers and/or multiple therapeutic agents.

The coating can be applied to the medical device by any known method in the art including dipping, spraying, rolling, brushing, electrostatic plating or spinning, vapor deposition, air spraying including atomized spray coating, and spray coating using an ultrasonic nozzle.

The coating is typically from about 1 to about 50 microns thick. In the case of balloon catheters, the thickness is preferably from about 1 to about 10 microns, and more preferably from about 2 to about 5 microns. Very thin polymer coatings, such as about 0.2-0.3 microns and much thicker coatings, such as more than 10 microns, are also possible. It is also within the scope of the present invention to apply multiple layers of polymer coatings onto the medical device. Such multiple layers may contain the same or different therapeutic agents and/or the same or different polymers.

The medical device may also contain a radio-opacifying agent within its structure to facilitate viewing the medical device during insertion and at any point while the device is implanted. Non-limiting examples of radio-opacifying agents are bismuth subcarbonate, bismuth oxychloride, bismuth trioxide, barium sulfate, tungsten, and mixtures thereof.

Although the present invention has been disclosed in detail, it should be understood that various changes, substitutions, and alterations may be made herein, the present invention is intended to cover various modifications and equivalent arrangements. Other examples may be made without departing from the spirit and scope of the present invention as defined by the following claims.

What is claimed is:

1. An injection device comprising:
a first catheter having a first catheter outer surface, a first catheter proximal end, a first catheter distal end and a first catheter inner surface to define a first catheter lumen extending between the first catheter proximal and distal ends;
a second catheter disposed in the first catheter lumen, said second catheter having a second catheter outer surface, a second catheter proximal end, a second catheter distal end and a second catheter inner surface to define a second catheter lumen extending between the second catheter proximal and distal ends;
a multiple delivery member injection device including an expandable member having a proximal wall, an opposing distal wall and a circumferential side wall connecting the proximal wall and the opposing distal wall, and a plurality of injection elements connected to the distal wall of the expandable member and an outer surface of the proximal wall of the expandable member being connected to the distal end of the second catheter to form a liquid tight seal, the expandable member being expandable to receive and hold a liquid under a positive pressure;
a third catheter disposed in the second catheter lumen, said third catheter having a third catheter outer surface, a third catheter proximal end, a third catheter distal end and a third catheter inner surface to define a third catheter lumen extending between the third catheter proximal and distal ends, the distal end of the third catheter being connected to the proximal wall of the expandable member; and
a plurality of filling tubes, each filling tube having a filling lumen proximal end, a filling tube distal end and a filling tube wall with an inner surface to define a filling tube lumen extending between the filling tube proximal and distal ends, the plurality of filling tubes being connected at their proximal ends to the distal end of the third catheter and the plurality of filling tubes being connected at their distal ends to the plurality of injection elements, the plurality of filling tubes to provide the therapeutic from the third catheter to the plurality of injection elements to produce a positive pressure in the plurality of injection elements,
each of the plurality of injection elements to hold the positively pressurized therapeutic until activated to release the therapeutic.

2. The injection device of claim 1 wherein each of the plurality of injection elements comprises:
a portion of the distal end of one of the filling tubes having a seal at the distal end to close the filling tube lumen and having defined in the filling tube wall a filling hole proximal of the seal;
a needle tip connected to the distal end of the filling tube, the needle tip having a sharp needle tip distal end, a needle tip proximal end, a needle tip wall having an inner surface to define a needle tip lumen extending between the needle tip proximal and distal ends and an exit hole in the needle tip wall distal of the seal;
a sliding cover co-axially aligned with and slidingly surrounding an area of the proximal end of the needle tip including the exit hole, the sliding cover to form a liquid-tight seal over the exit hole in a closed position and to permit fluid communication through the exit hole in an open position; and
a pressurizable capsule connected to the portion of the distal end of the filling tube proximal to the filling hole and connected to the proximal end of the needle tip distal to the exit hole and the sliding cover.

3. The injection device of claim 2 wherein the pressurizable capsule forms a liquid-tight seal around the portion of the distal end of the filling tube and the proximal end of the needle tip.

4. The injection device of claim 2 wherein the pressurizable capsule is connected at a distal end to a distal end of sliding seal.

5. The injection device of claim 4 wherein the pressurizable capsule is slidingly connected to the proximal end of the needle tip.

6. The injection device of claim 2 wherein the exit hole includes a valve to permit one-way fluid communication from the filling tube lumen into the pressurizable capsule.

7. The injection device of claim 6 wherein the pressurizable capsule includes an expandable material.

8. The injection device of claim 7 wherein the expandable material comprises a physiologically compatible elastic polymer.

9. The injection device of claim 2 wherein each pressurizable capsule is independently actuatable to release the therapeutic through the exit hole into the needle tip lumen.

10. The injection device of claim 9 wherein each pressurizable capsule is actuated to release the therapeutic by moving the sliding cover to the open position.

11. The injection device of claim 2 wherein each pressurizable capsule includes a pair of longitudinal folding sections.

12. The injection device of claim 11 wherein the longitudinal folding sections are on opposite sides of the pressurizable capsule.

13. The injection device of claim 11 wherein the longitudinal folding sections are to expand to receive the therapeutic.

14. The injection device of claim 2 wherein the sharp needle tip distal end is to penetrate a target tissue site.

15. The injection device of claim 1 wherein the expandable member comprises a physiologically compatible elastic polymer.

16. The injection device of claim 15 wherein the expandable member is to receive the liquid from the second catheter.

17. The injection device of claim 16 wherein the expandable member is to receive the liquid from the third catheter.

18. The injection device of claim 17 wherein the expandable member is to hold the liquid under the positive pressure after the plurality of injection elements have been activated to release the therapeutic.

19. The injection device of claim 15 wherein the expandable member is to receive the liquid from the second catheter.

20. An injection device comprising:
a first catheter having a first catheter outer surface, a first catheter proximal end, a first catheter distal end and a first catheter inner surface to define a first catheter lumen extending between the first catheter proximal and distal ends;
a second catheter disposed in the first catheter lumen, said second catheter having a second catheter outer surface, a second catheter proximal end, a second catheter distal end and a second catheter inner surface to define a second catheter lumen extending between the second catheter proximal and distal ends;
a multiple delivery member injection device including an expandable member having a proximal wall, an opposing distal wall and a circumferential side wall connecting the proximal wall and the opposing distal wall, and a plurality of injection elements connected to the distal wall of the expandable member and an outer surface of the proximal wall of the expandable member being connected to the distal end of the second catheter to form a liquid tight seal, the expandable member being expandable to receive and hold a liquid under a positive pressure from the second catheter;

a third catheter disposed in the second catheter lumen, said third catheter having a third catheter outer surface, a third catheter proximal end, a third catheter distal end and a third catheter inner surface to define a third catheter lumen extending between the third catheter proximal and distal ends, the distal end of the third catheter being connected to the proximal wall of the expandable member; and a plurality of filling tubes, each filling tube having a filling tube proximal end, a filling tube distal end and a filling tube wall with an inner surface to define a filling tube lumen extending between the filling tube proximal and distal ends, the plurality of filling tubes being connected at their proximal ends to the distal end of the third catheter and the plurality of filling tubes being connected at their distal ends to the plurality of injection elements, the plurality of filling tubes to provide the therapeutic from the third catheter to the plurality of injection elements to produce a positive pressure in the plurality of injection elements, each of the plurality of injection elements to hold the positively pressurized therapeutic until activated to release the therapeutic.

21. The injection device of claim 20 wherein each of the plurality of injection elements comprises:
a portion of the distal end of one of the filling tubes having a seal at the distal end to close the filling tube lumen; and
a needle tip slidingly disposed around the distal end of the filling tube distal end, the needle tip having a sharp needle tip distal end, a needle tip proximal end, a needle tip wall having an inner surface to define a needle tip lumen extending between the needle tip proximal and distal ends and a puncture tip connected to the proximal end of the needle tip, the puncture tip having a puncture tip distal end connected to the proximal end of the needle tip, a sharp puncture tip proximal end, a puncture tip wall having an inner surface to define a puncture tip lumen extending between the puncture tip proximal and distal ends and in fluid communication with the needle tip lumen.

22. The injection device of claim 21 wherein the sharp puncture tip is to penetrate the seal to put the filling tube lumen in fluid communication with the needle tip lumen when the needle tip is moved proximally to be against the seal.

23. The injection device of claim 22 wherein the sharp puncture tip is to be removed from the seal when the needle tip is moved distally away from the seal.

24. The injection device of claim 23 wherein the seal comprises a healable material that seals over after removal of the sharp puncture tip.

25. The injection device of claim 21 wherein the needle tip is biased away from the seal.

26. The injection device of claim 25 wherein the needle tip is moved proximally to puncture the seal with puncture tip when the needle tip is inserted into a target tissue site.

27. The injection device of claim 21 wherein the fill hole is to permit fluid communication between the filling tube lumen and the needle tip lumen when the fill hole is uncovered.

28. The injection device of claim 21 wherein the needle tip is biased away from the filling tube.

29. The injection device of claim 20 wherein each of the plurality of injection elements comprises:
a portion of the distal end of one of the filling tubes having a seal near the distal end to close the filling tube lumen; and
a needle tip slidingly disposed in the distal end of the filling tube distal to the seal, the needle tip having a sharp needle tip distal end, a needle tip proximal end, a needle tip wall having an inner surface to define a needle tip lumen extending between the needle tip proximal and distal ends and a puncture tip connected to the proximal end of the needle tip, the puncture tip having a puncture tip distal end connected to the proximal end of the needle tip, a sharp puncture tip proximal end, a puncture tip wall having an inner surface to define a puncture tip lumen extending between the puncture tip proximal and distal ends and in fluid communication with the needle tip lumen.

30. The injection device of claim 29 wherein the sharp puncture tip is to penetrate the seal to put the filling tube lumen in fluid communication with the needle tip lumen when the needle tip is moved proximally to be against the seal.

31. The injection device of claim 30 wherein the sharp puncture tip is to be removed from the seal when the needle tip is moved distally away from the seal.

32. The injection device of claim 31 wherein the seal comprises a healable material that seals over after removal of the sharp puncture tip.

33. The injection device of claim 20 wherein the needle tip is biased away from the seal.

34. The injection device of claim 33 wherein the needle tip is moved proximally to puncture the seal with puncture tip when the needle tip is inserted into a target tissue site.

35. The injection device of claim 20 wherein each of the plurality of injection elements comprises:
a portion of the distal end of the filling tube having an inner band seal circumferentially arranged around an inner wall of the filling tube; and
a needle tip slidingly disposed in the distal end of the filling tube distal end and the inner band seal, the needle tip having a sharp needle tip distal end, a closed needle tip proximal end, a needle tip wall having an inner surface to define a needle tip lumen extending between the needle tip proximal and distal ends, and a fill hole defined in the needle tip wall near the proximal end of the needle tip, the inner band seal being of sufficient size to seal the fill hole when positioned over the fill hole.

* * * * *